US010625732B2

(12) United States Patent
Kim et al.

(10) Patent No.: US 10,625,732 B2
(45) Date of Patent: Apr. 21, 2020

(54) APPARATUS AND METHOD FOR CONTROLLING AUTONOMOUS DRIVING OF VEHICLE, AND VEHICLE SYSTEM

(71) Applicants: Hyundai Motor Company, Seoul (KR); Kia Motors Corporation, Seoul (KR)

(72) Inventors: Jin Kwon Kim, Gyeonggi-do (KR); Sam Yong Kim, Gyeonggi-do (KR); Yu Jin Yun, Gyeonggi-do (KR); Seong Sook Ryu, Seoul (KR); Hwal Ly Lee, Seoul (KR); Byoung Joon Lee, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 243 days.

(21) Appl. No.: 15/806,510

(22) Filed: Nov. 8, 2017

(65) Prior Publication Data
US 2018/0297586 A1   Oct. 18, 2018

(30) Foreign Application Priority Data
Apr. 14, 2017   (KR) .......................... 10-2017-0048581

(51) Int. Cl.
*B60W 30/02*   (2012.01)
*A61B 5/053*   (2006.01)
(Continued)

(52) U.S. Cl.
CPC ........... *B60W 30/025* (2013.01); *A61B 3/112* (2013.01); *A61B 5/0205* (2013.01);
(Continued)

(58) Field of Classification Search
CPC ..... B60W 2540/22; B60W 2040/0872; B60W 2050/143; B60W 30/025; A61B 5/18; A61B 5/0531; B60Q 9/00
(Continued)

(56) References Cited

U.S. PATENT DOCUMENTS

2009/0040054 A1*   2/2009   Wang .................. B60W 30/095
                                                                340/576
2012/0025993 A1*   2/2012   Akiyama ................. A61B 5/18
                                                                340/576
(Continued)

FOREIGN PATENT DOCUMENTS

JP   2002-010995 A   1/2002
JP   2004-507308 A   3/2004
(Continued)

*Primary Examiner* — Isaac G Smith
(74) *Attorney, Agent, or Firm* — Mintz Levin Cohn Ferris Glovsky and Popeo, P.C.; Peter F. Corless (57) ABSTRACT

An apparatus and a method for controlling autonomous driving of a vehicle, and a vehicle system are provided. The apparatus monitors a stress state of a driver using biometric information of the driver and calculates an allowable jerk of the driver based on a jerk at a time point at which the stress state of the driver exceeds a preset reference value. A predicted jerk is calculated based on location and movement information of the vehicle and a preceding vehicle measured while the vehicle travels, and lane information. Additionally, a driving state of the vehicle is determined when the predicted jerk exceeds an allowable jerk of the driver and an alarm is output based on the driving state of the vehicle.

20 Claims, 6 Drawing Sheets

(51) Int. Cl.
  *B60Q 9/00* (2006.01)
  *G05D 1/00* (2006.01)
  *B60W 40/08* (2012.01)
  *B60W 50/14* (2020.01)
  *A61B 5/18* (2006.01)
  *A61B 5/0205* (2006.01)
  *A61B 3/11* (2006.01)
  *A61B 5/16* (2006.01)
  *A61B 5/00* (2006.01)
  *A61B 5/024* (2006.01)
  *G05D 1/02* (2020.01)

(52) U.S. Cl.
  CPC ........ *A61B 5/02405* (2013.01); *A61B 5/0531* (2013.01); *A61B 5/165* (2013.01); *A61B 5/18* (2013.01); *A61B 5/746* (2013.01); *B60Q 9/00* (2013.01); *B60W 40/08* (2013.01); *B60W 50/14* (2013.01); *G05D 1/0055* (2013.01); *G05D 1/021* (2013.01); *B60W 2040/0872* (2013.01); *B60W 2050/143* (2013.01); *B60W 2540/22* (2013.01)

(58) Field of Classification Search
  USPC .............................................. 701/27, 93, 96
  See application file for complete search history.

(56) References Cited

U.S. PATENT DOCUMENTS

2015/0360617 A1 12/2015 Schulz et al.
2016/0347293 A1* 12/2016 Chen ........................ B60T 7/22

FOREIGN PATENT DOCUMENTS

KR 10-1997-0036010 7/1997
KR 10-2015-0055052 A 5/2015

* cited by examiner

FIG. 1

| (a) | HRV | HEART RATE INCREASED |
| --- | --- | --- |
|  |  | HEART RATE VARIABILITY INCREASED |
| (b) | GSR | SIR FREQUENCY INCREASED |
| (c) | SIZE OF PUPIL | SIZE OF PUPIL INCREASED |

APPARATUS AND METHOD FOR CONTROLLING AUTONOMOUS DRIVING OF VEHICLE, AND VEHICLE SYSTEM

CROSS-REFERENCE TO RELATED APPLICATION

This application is based on and claims the benefit of priority to Korean Patent Application No. 10-2017-0048581, filed on Apr. 14, 2017, in the Korean Intellectual Property Office, the disclosure of which is incorporated herein in its entirety by reference.

TECHNICAL FIELD

The present disclosure relates to an apparatus and a method for controlling autonomous driving of a vehicle, and a vehicle system, and more particularly to an apparatus and method that control autonomous driving of a vehicle in which an allowable jerk is identified based on a change of a biometric signal during driving of the vehicle.

BACKGROUND

A jerk is a vector that indicates a time change rate of acceleration, may be represented by a third derivative of displacement and time, and may represent a forward and rearward vibration of a vehicle that occurs during an abrupt acceleration or gearshift of the vehicle. Recently, a jerk is used as an index for evaluating a riding quality of the driver. The driver operates the vehicle such that a jerk is not generated in a preferred or allowable range during an abrupt acceleration or gearshift. However, the ranges of preferred or allowable jerks are different for respective drivers during driving of vehicles.

Meanwhile, a collision control system of the vehicle performs a collision avoidance control by calculating a predicted collision time with a preceding vehicle. However, the conventional collision avoidance control does not consider a jerk of the driver which influences a riding quality of the driver and also affects the predicted collision time.

SUMMARY

The present disclosure provides an apparatus and a method for controlling autonomous driving of a vehicle, by which an allowable jerk may be determined based on a change of a biometric signal during driving of a driver and an autonomous driving control level may be determined based on the identified allowable jerk of the driver, and a vehicle system.

The present disclosure also provides an apparatus and a method for controlling autonomous driving of a vehicle, by which an alarm may be output when a predicted jerk of a driver calculated during driving of a vehicle with reference to an allowable jerk of the driver exceeds the allowable jerk of the driver, and a vehicle system. The technical objects of the present disclosure are not limited to the above-mentioned one, and the other unmentioned technical objects will become apparent to those skilled in the art from the following description.

In accordance with an aspect of the present disclosure, an apparatus for controlling autonomous driving of a vehicle may include a driver state monitoring device configured to monitor a stress state of a driver using biometric information of the driver, a jerk calculator configured to calculate an allowable jerk of the driver based on a jerk at a time point at which the stress state of the driver exceeds a preset reference value, and to calculate a predicted jerk based on location and movement information of the vehicle and a preceding vehicle measured while the vehicle is being driven, and lane information, a determination device configured to identify a driving state of the vehicle when the predicted jerk exceeds an allowable jerk of the driver, and an alarm processor configured to output an alarm based on the driving state of the vehicle.

In accordance with another aspect of the present disclosure, a method for controlling autonomous driving of a vehicle may include monitoring a stress state of a driver by using biometric information of a driver, calculating an allowable jerk of the driver based on a jerk at a time point at which the stress state of the driver exceeds a preset reference value, calculating a predicted jerk based on location and movement information of the vehicle and a preceding vehicle measured while the vehicle is being driven, and lane information, identifying a driving state of the vehicle when the predicted jerk exceeds an allowable jerk of the driver, and outputting an alarm based on a driving state of the vehicle.

In accordance with another aspect of the present disclosure, a vehicle system may include a detector having one or more sensors configured to measure a biometric signal of a driver, an autonomous driving control apparatus configured to monitor a stress state of the driver using the biometric information of the driver measured by the one or more sensors, to compare an allowable jerk of the driver calculated based on a jerk at a time point at which the stress state of the driver exceeds a preset reference value and a predicted jerk calculated based on location and movement information of the vehicle and the preceding vehicle measured while the vehicle is being driven, and to output an alarm signal based on a driving state of the vehicle when the predicted jerk exceeds the allowable jerk of the driver, and an interface configured to output information corresponding to the alarm signal.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Hereinafter, exemplary embodiments of the present disclosure will be described in detail with reference to the accompanying drawings. Throughout the specification, it is noted that the same or like reference numerals denote the same or like components even though they are provided in different drawings. Further, in the following description of the present disclosure, a detailed description of known functions and configurations incorporated herein will be omitted when it may make the subject matter of the present disclosure rather unclear.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

Furthermore, control logic of the present disclosure may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

In addition, terms, such as first, second, A, B, (a), (b) or the like may be used herein when describing components of the present disclosure. The terms are provided only to distinguish the elements from other elements, and the essences, sequences, orders, and numbers of the elements are not limited by the terms. In addition, unless defined otherwise, all terms used herein, including technical or scientific terms, have the same meanings as those generally understood by those skilled in the art to which the present disclosure pertains. The terms defined in the generally used dictionaries should be construed as having the meanings that coincide with the meanings of the contexts of the related technologies, and should not be construed as ideal or excessively formal meanings unless clearly defined in the specification of the present disclosure.

Figure 1:
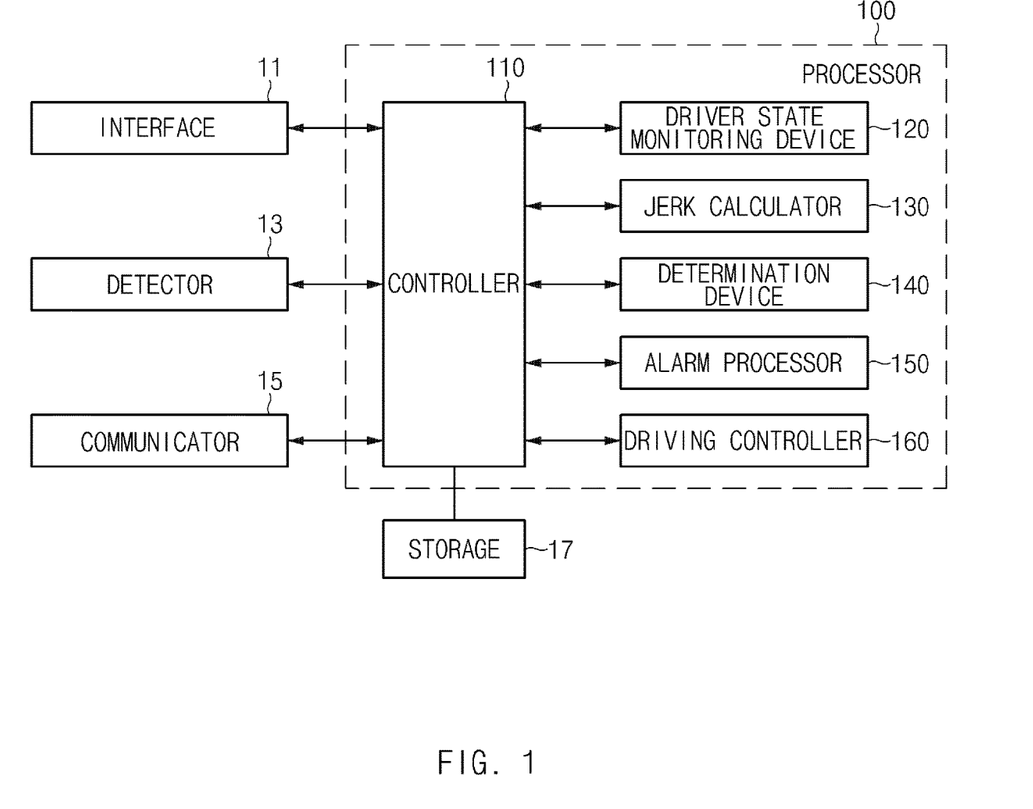
FIG. 1 is a block diagram illustrating a configuration of a vehicle system, to which an autonomous driving control apparatus is applied, according to an exemplary embodiment of the present disclosure.

FIG. 1 is a block diagram illustrating a configuration of a vehicle system, to which an autonomous driving control apparatus is applied, according to an exemplary embodiment of the present disclosure. Referring to FIG. 1, the vehicle system according to the exemplary embodiment of the present disclosure may include an interface E 11, a detector 13, a communication unit 15, a storage 13, and an autonomous driving control apparatus(processor) 100. A controller 110 may be configured to operate the components of the system as well as the autonomous driving control apparatus 100.

The apparatus 100 according to the present disclosure may be embodied in the interior of the vehicle. The autonomous driving control apparatus 100 may also be integrally formed with controllers mounted within the vehicle, or may be embodied as a separate apparatus to be connected to the controllers of the vehicle by a separate connection unit. In particular, the autonomous driving control apparatus 100 may be operated in association with an engine and a motor of the vehicle, and may be operated by a controller configured to operate the engine and the motor. The interface 11 may include an input unit configured to receive a control command, and an output unit configured to output an operation state and a result of the autonomous driving control apparatus 100.

Further, the input unit may include a key button, and may include a mouse, a joystick, a jog shuttle, and a stylus pen. The input unit may also include a soft key mounted on a display. The output unit may include a display, and may include a voice output unit such as a speaker. When a touch sensor, such as a touch film, a touch sheet, or a touch pad, is provided in the display, the display may be operated as a touch screen, and may be embodied in a form in which an input unit and an output unit are integrated. The display may also include at least one of a liquid crystal display (LCD), a thin film transistor-liquid crystal display (TFT-LCD), an organic light-emitting diode (OLED), a flexible display, a field emission display (FED), and a 3D display.

The detector 13 may include one or more sensors configured to measure biometric signals of the driver. For example, the detector 13 may include a first sensor configured to measure a heart rate state of the driver, a second sensor configured to measure a galvanic skin response of skin of the driver, and a third sensor configured to measure the size of a pupil of the driver (e.g., the size adjustment of the pupil). Additionally, the detector 13 may be configured to measure biometric information of the driver when a preset event occurs, and provide the measured biometric information of the driver to the autonomous driving control apparatus 100. The detector 13 may include one or more sensors configured to detect an obstacle located around the vehicle, for example, a preceding vehicle 20 located in front of the vehicle, and measure a distance from the corresponding obstacle. The detector 13 may further include a sensor configured to measure a velocity and/or an acceleration of the vehicle. The event comprise a stress state of the driver. The stress state of the driver is determined based on biometric information (a galvanic skin response (GSR), a size of a pupil of the driver, a heart rates of the driver etc).

The communication unit 15 may include a communication module that supports a communication interface with electronic components and/or controllers mounted within the vehicle. For example, the communication module may be configured to transmit the biometric information of the driver measured by the detector 13 to the autonomous driving control apparatus 100, and may be configured to transmit an operation state and a result of the autonomous driving control apparatus 100 to the interface 11 and/or the storage 17. In particular, the communication module may include a module that supports network communication of the vehicle, such as controller area network (CAN) communication, local interconnect network (LIN), or Flex-Ray communication. The communication module may also include a module for wireless Internet connection or short range communication. Accordingly, the communication unit 15 may be configured to perform vehicle to vehicle (V2V) communication with another vehicle surrounding the subject vehicle, for example, a preceding vehicle. Then, the communication unit 15 may be configured to receive information regarding the preceding vehicle, for example, location, velocity, and acceleration information of the preceding vehicle, via the V2V communication with the preceding vehicle.

Further, the storage 17 may be configured to store data and/or algorithms that are necessary for operating the autonomous driving control apparatus 100. For example, the storage 17 may be configured to store the biometric information of the driver measured by the detector 13, and store information regarding the preceding vehicle received by the communication unit 15. Further, the storage 17 may be configured to store a setting condition for an operation of the autonomous driving control apparatus 100, and an operation result. The storage 17 may also be configured to store an algorithm used to calculate a jerk and determine a state of the driver by the autonomous driving control apparatus 100, and store a command for operating the vehicle according to the determination of the autonomous driving control apparatus 100.

Although the embodiment of FIG. 1 illustrates that the storage 17 is provided separately from the autonomous driving control apparatus 100, a separate storage device may be embodied in the interior of the autonomous driving control apparatus 100. In particular, the storage 17 may include storage media, such as a random access memory (RAM), a static random access memory (SRAM), a read-only memory (ROM), a programmable read-only memory (PROM), and an electrically erasable programmable read-only memory.

Figure 2:
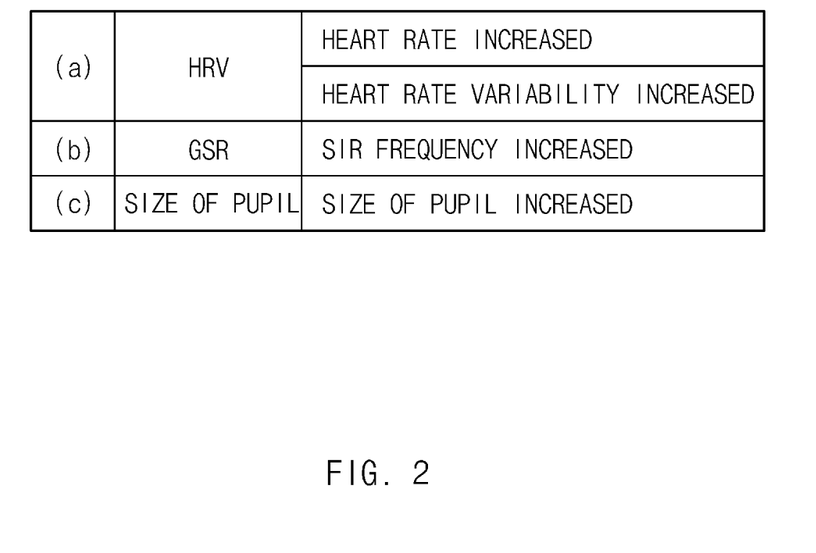
FIGS. 2 to 4 are views illustrating an operation of the autonomous driving control apparatus according to the exemplary embodiment of the present disclosure.

The autonomous driving control apparatus 100 may be configured to detect a state of the driver using the biometric information of the driver measured by the detector 13, and determine an autonomous driving control level by calculating an allowable jerk and a predicted jerk of the driver in response to determining that the driver is in a stress state. The autonomous driving control apparatus 100 may include a controller 110, a driver state monitoring device 120, a jerk calculator 130, a determination device 140, an alarm processor 150, and a driving controller 160. In particular, the controller 110 may be configured to process signals delivered between the elements of the autonomous driving control apparatus 100. The driver state monitoring device 120 may be configured to monitor a stress state of the driver using biometric information of the driver measured by the detector 13, for example, a heart rate state, a galvanic skin response, and/or the size of a pupil. The driver state monitoring device 120 may be configured to identify a stress state of the driver based on the conditions illustrated in FIG. 2.

For example, as illustrated in FIG. 2A, the driver state monitoring device 120 may be configured to determine a stress state of the driver based on a heart rate variability (HRV) of the driver. In particular, when the heart rates of the driver increases by a specific range (or a specific ratio) or greater and the heart rate variability (HRV, LF/HF) increases by a specific range (or a specific ratio) or greater, the driver state monitoring device 120 may be configured to determine that the stress index of the driver exceeds a reference value A.

Meanwhile, as illustrated in FIG. 2B, the driver state monitoring device 120 may be configured to determine a stress state of the driver based on a galvanic skin response (GSR) of the skin of the driver. In particular, when a skin impedance response (SIR) frequency of the driver increases by a specific range (or a specific ratio) or greater, the driver state monitoring device 120 may be configured to determine that the stress index of the driver exceeds a preset reference value A.

Additionally, as illustrated in FIG. 2C, the driver state monitoring device 120 may be configured to determine a stress state of the driver based on the size of a pupil of the driver. In particular, when the size of a pupil of the driver increases by a specific range (or a specific ratio) or greater, the driver state monitoring device 120 may be configured to determine that the stress index of the driver exceeds a reference value A. Of course, the driver state monitoring device 120 may be configured to determine that the stress index of the driver exceeds the reference value A when all the three conditions illustrated in FIGS. 2A to 2C or two or more of them are satisfied.

The jerk calculator 130 may be configured to measure a jerk while the vehicle travels. In particular, the jerk is a vector that designates a time change rate of an acceleration of the vehicle, and may be represented by a third derivative of displacement and time. For example, the jerk may be represented by a value that is a derivative of an acceleration in a corresponding zone when the vehicle 10 starts at a start time point and stops at an end time point. In particular, the end time point refers to a time point at which the vehicle stops at a location shortly before the vehicle collides with a preceding vehicle located on the front side of the vehicle or a time point shortly before the vehicle deviates from a lane.

Further, in response to determining that the stress index of the driver exceeds the preset reference value A, the jerk calculator 130 may be configured to store a minimum jerk measured at the corresponding time point and determine the minimum jerk as an allowable jerk of the driver. Then, the driving controller 160 may be configured to determine an autonomous driving control level based on the determined allowable jerk. In particular, the driving controller 160 may be configured to determine the autonomous driving control level by a level that maintains a jerk that is less than the determined allowable jerk. Further, the jerk calculator 130 may be configured to calculate a predicted jerk while the vehicle travels after the allowable jerk of the driver is determined. Then, the jerk calculator 130 may be configured to calculate a predicted longitudinal jerk for preventing the vehicle from colliding with a preceding vehicle and a predicted transverse jerk for preventing the vehicle from deviating from a lane.

Exemplary Embodiment of Calculating a Predicted Longitudinal Jerk

Figure 3:
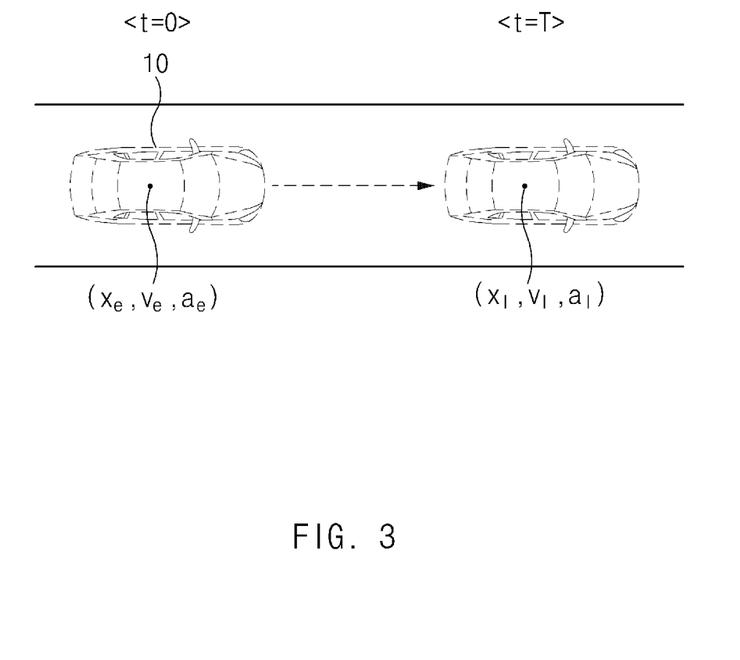

First, a technology of calculating a predicted longitudinal jerk will be described with reference to FIG. 3. As illustrated in FIG. 3, when a longitudinal location, a longitudinal velocity, and a longitudinal acceleration of the vehicle 10 at the current time point are xe, ve, and ae and a location, a velocity, and an acceleration of the preceding vehicle 20 at the same time point are xl, vl, and a predicted longitudinal jerk in a section between the vehicle 10 and the preceding vehicle 20 may be calculated by using xe, ve, and ae and xl, vl, and al. Then, a movement condition of the vehicle 10 for the predicted longitudinal jerk in the corresponding section may be represented as in Equation 1.

$$x(t) = \sum_{k=0}^{5} a_k t^k \qquad \text{Equation 1}$$

wherein, x(t) is a longitudinal location of the vehicle 10 at a time point t, t is a time point, and ak is an arbitrary coefficient. When it is assumed that the start time point with reference to the current location of the vehicle 10 is 0 and a time point shortly before the vehicle 10 collides with the preceding vehicle 10, that is, the end time point is T, x(0) represents a longitudinal location of the vehicle 10 at the start time point, that is, the current location (hereinafter, referred to as 'a first location') and x(T) represents a longitudinal location of the vehicle 10 at the end time point T (hereinafter, referred to as "a second location"). Additionally, x(0) is the longitudinal location at the start time point of the vehicle 10 and thus may be 0.

Further, the longitudinal velocity of the vehicle 10 at the start time point (t=0) (hereinafter, 'a first velocity') may be represented by x'(0) and the longitudinal acceleration (hereinafter, 'a first acceleration) may be represented by x"(0), and the longitudinal velocity of the vehicle 10 at the end time point (t=T) (hereinafter, referred to as 'a second velocity') may be represented by x'(T) and the longitudinal acceleration (hereinafter, 'a second acceleration') may be represented by x"(T).

Particularly, according to the present disclosure, a predicted longitudinal jerk may be calculated in a condition in which the vehicle stops when the end time point is reached. Accordingly, the vehicle has to be in a stop state at the end time point, x'(T) that is the second velocity and x"(T) that is the second acceleration have a value of 0. The jerk calculator 130 may be configured to derive a0=x(0) by applying t=0 to x(t) of Equation 1. Further, the jerk calculator 130 may be configured to derive a1=x'(0) by applying t=0 to x'(t) of Equation 1. The jerk calculator 130 may also be configured to derive a2=x"(0)/2 by applying t=0 to x"(t) that is a derivative of x'(t). Lastly, the jerk calculator 130 may be configured to derive x(T), x'(T), and x"(T) by applying t=T to x(t), x'(t), and x"(t) of Equation 1.

Meanwhile, the vehicle 10 stops at a time point shortly before the vehicle 10 collides with the preceding vehicle 20, that is, the end time point, the preceding vehicle 20 may be in a driving state or may be in a stop state. Under the assumption that the preceding vehicle 20 maintains a movement state of the start time point when the preceding vehicle 20 is in a driving state at the end time point, the velocity vl and the acceleration al of the preceding vehicle 20 may be vl+alT>0. In particular, the second location of the vehicle 10 may be represented as in Equation 2.

$$x(T) = x_l + v_l T + \frac{1}{2} a_l T^2 \qquad \text{Equation 2}$$

Meanwhile, under the assumption that the preceding vehicle 20 maintains a movement state of the start time point when the preceding vehicle 20 is in a stop state at the end time point, the velocity vl and the acceleration al of the preceding vehicle 20 may be vl+alT≤0. In particular, the second location of the vehicle 10 may be represented as in Equation 3.

$$x(T) = x_l - \left(\frac{v_l^2}{2a_l}\right) \qquad \text{Equation 3}$$

As discussed above, since the vehicle 10 stops at the end time point, the jerk at the end time point may be 0. Accordingly, the jerk calculator 130 may be configured to calculate a time point at which a third derivative x(t)''' of x(t) of Equation 1 is 0. When x'''(t) is arranged by T using Equation 2 representing the second location x(T) of the vehicle 10 under the assumption that the preceding vehicle 20 is in a driving state at the end time point, the end time point Tmov at which the vehicle 10 stops may be represented as in Equations 4 and 5.

$$T_{mov} = \frac{4v_e - 10v_l + 2\sqrt{\begin{array}{c}25v_l^2 - 20v_l v_e + \\ 4v_e^2 - 50a_l x_l + 5a_e x_l\end{array}}}{10a_l - a_e} \qquad \text{Equation 4}$$

$$T_{mov} = \frac{4v_e - 10v_l - 2\sqrt{\begin{array}{c}25v_l^2 - 20v_l v_e + \\ 4v_e^2 - 50a_l x_l + 5a_e x_l\end{array}}}{10a_l - a_e} \qquad \text{Equation 5}$$

Meanwhile, when x'''(t) is arranged by T by using Equation 3 representing the second location x(T) of the vehicle 10 under the assumption that the preceding vehicle 20 is in a stop state at the end time point, the end time point Tstop at which the vehicle 10 stops may be represented as in Equations 6 and 7.

$$T_{stop} = \frac{-4a_l v_e + \sqrt{16a_l^2 v_e^2 + 20a_e x_l a_l^2 - 10a_e a_l v_l^2}}{a_l a_e} \qquad \text{Equation 6}$$

$$T_{stop} = \frac{-4a_l v_e - \sqrt{16a_l^2 v_e^2 + 20a_e x_l a_l^2 - 10a_e a_l v_l^2}}{a_l a_e} \qquad \text{Equation 7}$$

Particularly, the jerk calculator 130 may be configured to determine Tmov, which is less than a stop time point −(vl/al) of the preceding vehicle 20, among Tmovs of Equations 4 and 5, as the end time point T. When both of Tmovs of Equations 4 and 5 are greater than the stop time point −(vl/al) of the preceding vehicle 20, the jerk calculator 130 may be configured to determine Tstop, which is a positive number and the smallest, among the Tstops of Equations 6 and 7 as an end time point T. Then, the determined end time point T may be defined as a first end time point. When the first end time point T is determined via the above-mentioned process, the jerk calculator 130 may be configured to calculate a jerk, an absolute value of which is greatest among the predicted jerks generated in a section from the start time point t=0 to the determined first end time point t=T, as a predicted longitudinal jerk.

Exemplary Embodiment of Calculating a Predicted Transverse Jerk

Figure 4:
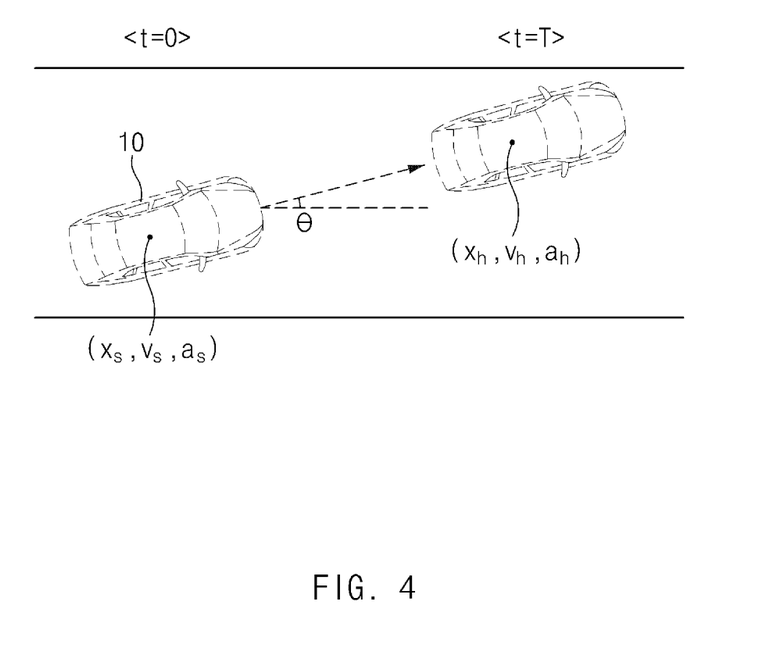

Meanwhile, a technology of calculating a predicted transverse jerk will be described with reference to FIG. 4. When a transverse location, a transverse velocity, a transverse acceleration of the vehicle at the start time point t=0, that is, the current time point are xs, vs, and as and a transverse location, a transverse velocity, a transverse acceleration of the vehicle 10 at the end time point t=T, that is, at a time point shortly before the vehicle intrudes a line (or a time point shortly before the vehicle deviates from a lane) are xh, vh, and ah as illustrated in FIG. 4, a predicted transverse jerk in the section between the vehicle 10 and the line may be calculated by using xs, vs, and as, and xh, vh, and ah.

Further, the transverse location xs of the vehicle at the start time point (hereinafter, referred to as 'a third location') may be calculated by subtracting a half of the width of the vehicle from an output value of a front side monitoring camera (e.g., an MFC) configured to monitor intrusion of a line by the vehicle (e.g., the vehicle crossing a road lane line). Further, the transverse velocity vs of the vehicle 10 at the start time point (hereinafter, referred to as 'a third velocity') may be calculated using Equation 8.

$$v_s = v \times \sin \theta \quad \text{(Equation 8)}$$

In Equation 8, v is a velocity of the vehicle and θ is a heading angle of the vehicle.

Further, the transverse acceleration as of the vehicle 10 at the start time point (hereinafter, referred to as 'a third acceleration') may be calculated using a derivative of the third velocity, that is, as=vs'=dvs/dt. Hereinafter, the transverse location xs of the vehicle at the end time point will be referred to as 'a fourth location', the transverse vs will be referred to as 'a fourth velocity', and the transverse acceleration as will be referred to as 'a fourth acceleration'.

The vehicle has to be in a stop state shortly before it intrudes a line. Accordingly, the fourth velocity and the fourth acceleration have a value of 0. Then, the movement condition of the vehicle 10 for the predicted transverse jerk in the section between the vehicle 10 and the lane is a movement condition of the vehicle 10 for a predicted longitudinal jerk in a section between the vehicle 10 and a preceding vehicle, and is as in Equation 1. Referring to Equation 1, the third location may be x(0), the third velocity may be x'(0), and the third acceleration may be x"(0), and the fourth location may be x(T), the fourth velocity may be x'(T), and the fourth acceleration may be x"(T). Then, x'(T) and x"(T) have a value of 0.

As discussed above, since the vehicle 10 stops at the end time point, the jerk at the end time point may be 0. Accordingly, the jerk calculator 130 may be configured to calculate a time point at which a third derivative x(t)''' of x(t) of Equation 1 becomes 0, that is, an end time point. Since the vehicle 10 has to be in a stop state at the end time point, if x'''(T) is derived from Equation 1 and is arranged with respect to T, the end time point T at which the vehicle stops may be represented as in Equations 9 and 10.

$$T = \frac{-4v_s + 2\sqrt{4v_s^2 - 5a_s x_s}}{a_s} \quad \text{Equation 9}$$

$$T = \frac{-4v_s - 2\sqrt{4v_s^2 - 5a_s x_s}}{a_s} \quad \text{Equation 10}$$

When both two Ts calculated by reflecting the third location, the third velocity, and the third acceleration reflected in Equations 9 and 10 are positive values, the smaller one of the two Ts may be determined as an end time point, and only any one of the two Ts is a positive value, the T that is a positive value may be determined as an end time point. Meanwhile, when both the two Ts calculated from Equations 9 and 10 are negative values, the largest one of the two Ts may be determined as an end time point. Then, the determined end time point T may be defined as a second end time point.

When the second end time point T is determined via the above-mentioned process, the jerk calculator 130 may be configured to calculate a jerk, an absolute value of which is the larger value among the predicted jerks generated in a section from the start time point t=0 to the determined second end time point t=T, as a predicted transverse jerk. In particular, the jerk calculator 130 may be configured to compare the predicted longitudinal jerk and the predicted transverse jerk, which have been calculated above. Then, the jerk calculator 130 may be configured to determine a jerk, which has the greatest value of the predicted longitudinal jerk and the predicted transverse jerk, as a predicted jerk.

In other words, the jerk calculator 130 may be configured to determine that the predicted transverse jerk increases the stress index of the driver when the predicted longitudinal jerk is greater than the predicted transverse jerk. Accordingly, the jerk calculator 130 may be configured to determine the predicted longitudinal jerk as a predicted jerk. Meanwhile, the jerk calculator 130 may be configured to determine that the predicted transverse jerk increases the stress index of the driver when the predicted transverse jerk is greater than the predicted longitudinal jerk. Accordingly, the jerk calculator 130 may be configured to determine the predicted longitudinal jerk as a predicted jerk. The determination device 140 may be configured to determine whether the determined predicted jerk exceeds an allowable jerk of the driver. When the predicted jerk exceeds the allowable jerk of the driver, the determination device DEVICE 140 may be configured to determine whether the vehicle is in an autonomous driving state. The alarm processor 150 may be configured to output an alarm signal to the interface 11 of the vehicle in response to determining that the predicted jerk exceeds the allowable jerk of the driver while the vehicle is in an autonomous driving state.

Meanwhile, when the vehicle is not in an autonomous driving state, the determination 140 may be configured to determine a driving manipulation state of the driver. In response to determining that a separation driving manipulation of the driver is not detected when the predicted jerk exceeds the allowable jerk of the driver, the alarm processor 150 may be configured to output an alarm signal to the interface 11. In response to determining that a separate driving manipulation of the driver is not detected when the predicted jerk exceeds the allowable jerk of the driver, the driving controller 160 may be configured to activate an autonomous driving control of the driver to prevent a potential collision or accident. Additionally, in response to determining that a separate driving manipulation of the driver is detected, the alarm processor 150 may be configured to determine that the level of the riding quality is abnormal and output a riding quality level abnormality signal and an alarm signal to the interface 11 of the vehicle.

Figure 5:
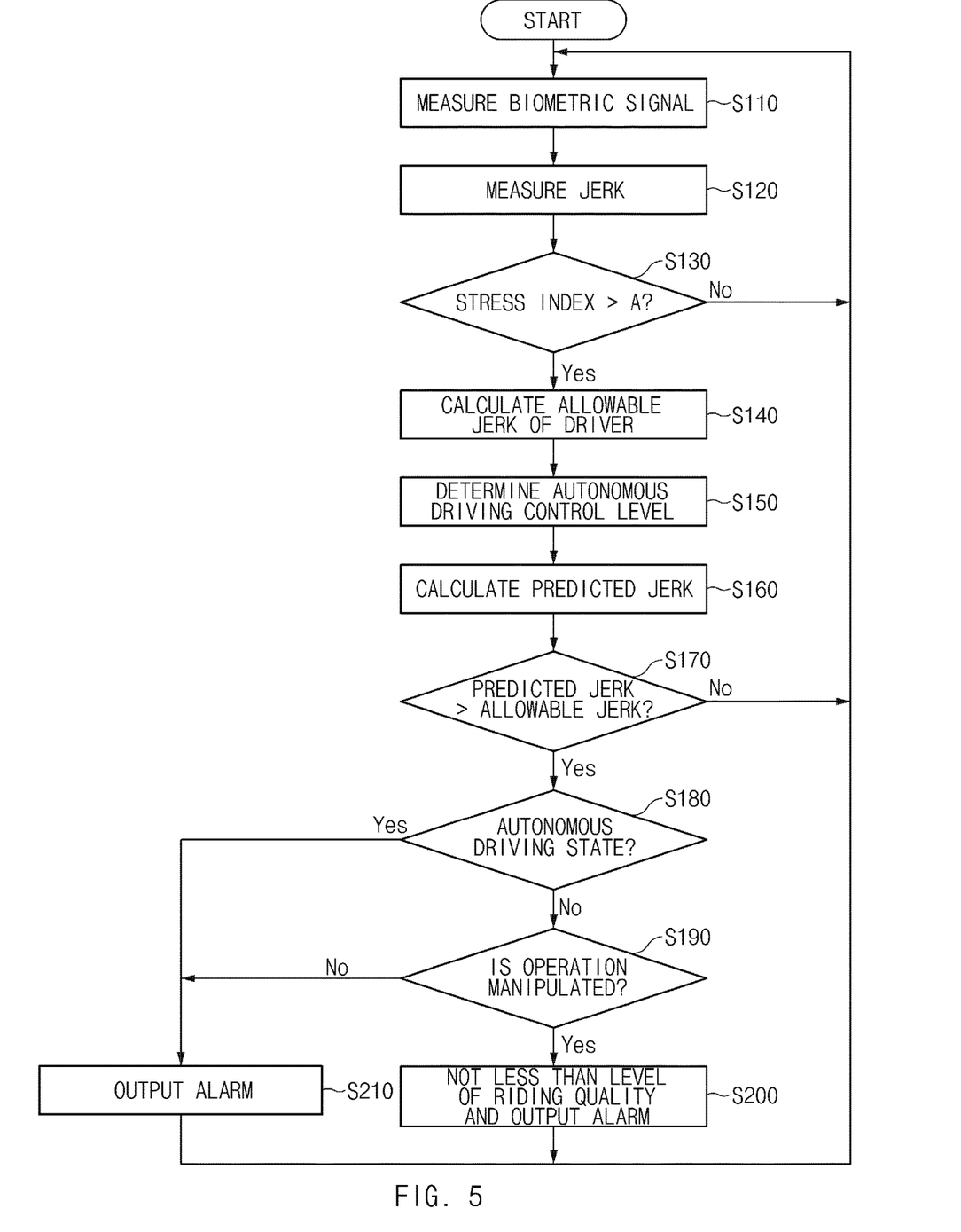
FIG. 5 is a view illustrating a flow of operations for an autonomous driving control method according to an exemplary embodiment of the present disclosure.

An operational flow of the apparatus for controlling autonomous driving of the vehicle according to the present disclosure will be described in detail. FIG. 5 is a view illustrating a flow of operations for an autonomous driving control method according to an exemplary embodiment of the present disclosure. The method described herein below may be executed by a processor within the apparatus.

Referring to FIG. 5, the autonomous driving control apparatus 100 may be configured to acquire biometric information of the driver measured from the sensors in the vehicle while the vehicle travels (S110), and measure a jerk of the driver (S120). In operation 'S110', the autonomous driving control apparatus may be configured to acquire heart rate information, galvanic skin response information and/or pupil size information of the driver, and determine whether the stress index of the driver exceeds a preset reference value A based on the acquired biometric information of the driver. In particular, the autonomous driving control apparatus may be configured to determine whether the stress index of the driver exceeds the preset reference value based on the heart rate of the driver, an increment of the heat rate variability, an increment of a skin impedance reflection rate, and/or an increment of the size of a pupil.

In response to determining that the stress index of the driver exceeds the preset reference value A (S130), the autonomous driving control apparatus 100 may be configured to calculate a minimum jerk measured at a time point at which the stress index exceeds the preset reference value A as the allowable jerk of the driver (S140). Then, the autonomous driving control apparatus 100 may be configured to determine a level at which a jerk that is less than the allowable jerk of the drive calculated in operation 'S140' may be maintained as an autonomous driving control level (S150). Thereafter, the autonomous driving control apparatus 100 may be configured to calculate a predicted jerk while the vehicle travels (S160).

In operation 'S160', the autonomous driving control apparatus 100 may be configured to calculate a predicted longitudinal jerk generated in a section until the vehicle 10 reaches a location of a preceding vehicle based on location and movement information of the vehicle 10 and the preceding vehicle measured while the subject vehicle is being driven. Further, the autonomous driving control apparatus 100 may be configured to calculate a predicted transverse jerk generated in a section until the vehicle 10 reaches a location of a line based on location and movement information of the vehicle 10 measured while the vehicle 10 travels, and lane information. Then, the autonomous driving control apparatus 100 may be configured to calculate the larger one of the predicted longitudinal jerk and the predicted transverse jerk, calculated as a predicted jerk. Accordingly, the description of FIGS. 3 and 4 will be referenced for the process of calculating the predicted longitudinal jerk and the predicted transverse jerk.

The autonomous driving control apparatus 100 may then be configured to compare the allowable jerk of the driver calculated in operation 'S140' and the predicted jerk calculated in operation 'S160'. When the predicted jerk is greater than the allowable jerk of the driver (S170), the autonomous driving control apparatus 100 may be configured to determine whether the vehicle is in an autonomous driving state, and when the vehicle is in an autonomous driving state (S180), the autonomous driving control apparatus 100 may be configured to output an alarm signal (S210).

Meanwhile, when the vehicle is not in an autonomous driving state (S180), the autonomous driving control apparatus 100 may be configured to determine whether there is a driving manipulation of the driver. When there is no driving manipulation of the driver (S190), the autonomous driving control apparatus 100 may be configured to output an alarm signal (S210). Additionally, when there is a driving manipulation (S190), the autonomous driving control apparatus 100 may be configured to determine that the level of the riding quality is abnormal and output a riding quality level abnormality state and an alarm (S200).

The autonomous driving control apparatus 100 according to the present exemplary embodiment may include one or more processors and memories. Additionally, the controller 110, the driver state monitoring device 120, the jerk calculator 130, the determination device 140, and the alarm processor 150 of the autonomous driving control apparatus 100 may be embodied in forms of independent hardware devices, and the one or more processors may be driven in a form in which the processors are included in other hardware devices, such as microprocessors or general-purpose computer systems.

Figure 6:
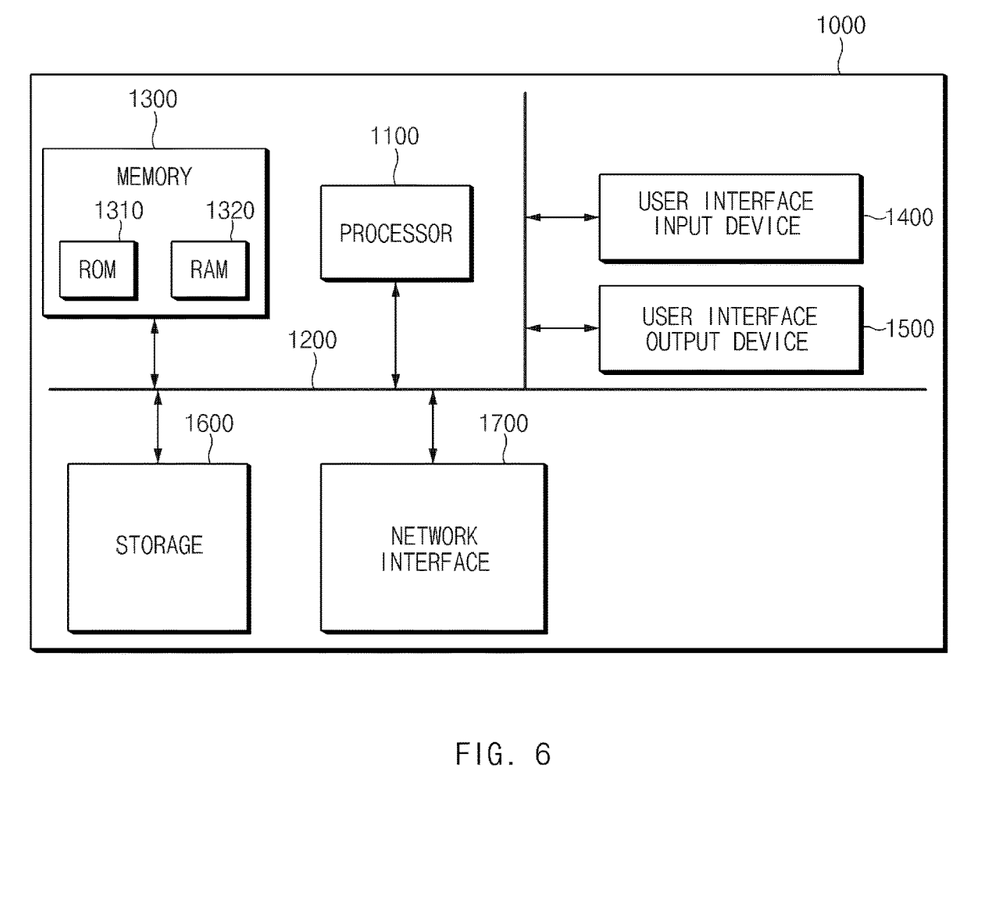
FIG. 6 is a block diagram illustrating a computing system that executes the method according to an exemplary embodiment of the present disclosure.

FIG. 6 is a block diagram illustrating a computing system that executes an autonomous driving control method according to an exemplary embodiment of the present disclosure. Referring to FIG. 6, the computing system 1000 may include at least one processor 1100 connected via a bus 1200, a memory 1300, a user interface input device 1400, a user interface output device 1500, a storage 1600, and a network interface 1700. The processor 1100 may be a central processing unit (CPU) or a semiconductor device that processes instructions stored in the memory 1300 and/or the storage 1600. The memory 1300 and the storage 1600 may include various volatile or nonvolatile storage media. For example, the memory 1300 may include a read only memory (ROM) and a random access memory (RAM).

Accordingly, the steps of the method or algorithm described in relation to the exemplary embodiments of the present disclosure may be implemented directly by hardware executed by the processor 1100, a software module, or a combination thereof. The software module may reside in a storage medium (e.g., the memory 1300 and/or the storage 1600), such as a RAM memory, a flash memory, a ROM memory, an EPROM memory, an EEPROM memory, a register, a hard disk, a detachable disk, or a CD-ROM. The exemplary storage medium may be coupled to the processor 1100, and the processor 1100 may be configured to read information from the storage medium and write information in the storage medium. In another method, the storage medium may be integrated with the processor 1100. The processor and the storage medium may reside in an application specific integrated circuit (ASIC). The ASIC may reside in a user terminal. In another method, the processor and the storage medium may reside in the user terminal as an individual component.

According to the present disclosure, an allowable jerk may be identified based on a change of a biometric signal during driving of a driver and an autonomous driving control level may be determined based on the identified allowable jerk of the driver, making it possible to improve the riding quality of the driver. Further, according to the present disclosure, an alarm may be output when a predicted jerk of a driver calculated during driving of a vehicle with reference to an allowable jerk of the driver exceeds the allowable jerk of the driver.

The above description is a simple exemplification of the technical spirit of the present disclosure, and the present disclosure may be variously corrected and modified by those skilled in the art to which the present disclosure pertains without departing from the essential features of the present disclosure. Therefore, the disclosed exemplary embodiments of the present disclosure do not limit the technical spirit of the present disclosure but are illustrative, and the scope of the technical spirit of the present disclosure is not limited by the exemplary embodiments of the present disclosure. The scope of the present disclosure should be construed by the claims, and it will be understood that all the technical spirits within the equivalent range fall within the scope of the present disclosure.

What is claimed is:

1. An apparatus for controlling autonomous driving of a vehicle, comprising:
a memory configured to store program instructions; and
a processor configured to execute the program instructions, the program instructions when executed configured to:
monitor a stress state of a driver using biometric information of the driver;
calculate an allowable jerk of the driver based on a jerk at a time point at which the stress state of the driver exceeds a preset reference value, and to calculate a predicted jerk based on location and movement information of the vehicle and a preceding vehicle measured while the vehicle travels, and lane information;
determine a driving state of the vehicle when the predicted jerk exceeds the allowable jerk of the driver; and
output an alarm according to the driving state of the vehicle.

2. The apparatus of claim 1, wherein the biometric information of the driver includes at least one selected from the group consisting of: a heart rate, a heart rate variability, a skin impedance response, and a size of a pupil of the driver.

3. The apparatus of claim 2, wherein, when any one of the heart rate, the heart rate variability, the skin impedance response, and the size of the pupil of the driver increases by a specific range or ratio or more, the program instructions when executed are configured to determine that the stress state of the driver exceeds the preset reference value.

4. The apparatus of claim 2, wherein, when two or more of the heart rate, the heart rate variability, the skin impedance response, and the size of the pupil of the driver increase by a specific range or ratio or more, the program instructions when executed are configured to determine that the stress state of the driver exceeds the preset reference value.

5. The apparatus of claim 1, wherein the program instructions when executed are configured to calculate a jerk by obtaining a third derivative of the location of the vehicle.

6. The apparatus of claim 1, wherein the program instructions when executed are configured to calculate a jerk while the vehicle travels, and calculate a minimum jerk calculated at a time point at which the stress state of the driver exceeds the preset reference value as the allowable jerk of the driver.

7. The apparatus of claim 1, wherein the program instructions when executed are configured to calculate a predicted longitudinal jerk and a predicted transverse jerk generated in a section until the vehicle reaches the location of the preceding vehicle and the location of a line based on location and movement information of the vehicle and the preceding vehicle measured while the vehicle travels and the lane information.

8. The apparatus of claim 7, wherein the program instructions when executed are configured to calculate a time point at which a predicted jerk generated in the section until the vehicle reaches the location of the preceding vehicle is 0 based on location, velocity, and acceleration information of the vehicle and location, velocity, and acceleration information of the preceding vehicle, and determines the time point at which the predicted jerk is 0 as a first end time point.

9. The apparatus of claim 8, wherein the program instructions when executed are configured to calculate a jerk, an absolute value of which is larger among predicted jerks generated in a section between a start time point and the first end time point while a current time point is taken as the start time point, as a predicted longitudinal jerk.

10. The apparatus of claim 7, wherein the program instructions when executed are configured to calculate a time point at which a predicted jerk generated in the section until the vehicle reaches the location of a line is 0 based on location, velocity, acceleration, and heading angle information of the vehicle and location information of the lane, and determine the time point at which the predicted jerk is 0 as a second end time point.

11. The apparatus of claim 10, wherein the program instructions when executed are configured to calculate a jerk, an absolute value of which is larger among predicted jerks generated in a section between the start time point and the second end time point while the current time point is taken as the start time point, as a predicted transverse jerk.

12. The apparatus of claim 7, wherein the program instructions when executed are configured to determine the larger one of the predicted longitudinal jerk and the predicted transverse jerk as a predicted jerk.

13. The apparatus of claim 1, wherein the program instructions when executed are configured to determine whether the vehicle is in an autonomous driving state when the predicted jerk exceeds the allowable jerk of the driver, and output an alarm when the vehicle is in an autonomous driving state.

14. The apparatus of claim 1, wherein the program instructions when executed are configured to determine whether driving of the vehicle is manipulated when the vehicle is not in an autonomous driving state when the predicted jerk exceeds the allowable jerk of the driver, and output an alarm when driving of the vehicle is not manipulated.

15. The apparatus of claim 14, wherein an abnormal state of a riding quality of the vehicle is output and an alarm is output when driving of the vehicle is manipulated.

16. The apparatus of claim 1, wherein the program instructions when executed are configured to determine an autonomous driving control level of the vehicle based on the allowable jerk of the driver.

17. A method for controlling autonomous driving of a vehicle, comprising:
monitoring, by a processor, a stress state of a driver using biometric information of a driver;
calculating, by the processor, an allowable jerk of the driver based on a jerk at a time point at which the stress state of the driver exceeds a preset reference value;
calculating, by the processor, a predicted jerk based on location and movement information of the vehicle and a preceding vehicle measured while the vehicle is being driven, and lane information;
determining, by the processor, a driving state of the vehicle when the predicted jerk exceeds the allowable jerk of the driver; and
outputting, by the processor, an alarm based on a driving state of the vehicle.

18. The method of claim 17, wherein the calculating of the predicted jerk includes:
calculating, by the processor, a predicted longitudinal jerk generated in a section until the vehicle reaches the location of the preceding vehicle based on location, velocity, and acceleration information of the vehicle, and location, velocity, and acceleration information of the preceding vehicle;

calculating, by the processor, a predicted transverse jerk generated in a section until the vehicle reaches the location of the lane based on location, velocity, acceleration, and heading angle information of the vehicle, and location information of the lane; and determining, by the processor, a larger one of the predicted longitudinal jerk and the predicted transverse jerk as a predicted jerk.

19. The method of claim 17, further comprising:

after the calculating of the allowable jerk of the driver, determining, by the processor, an autonomous driving control level of the vehicle based on the allowable jerk of the driver.

20. A vehicle system comprising:

a detector including one or more sensors configured to measure a biometric signal of a driver;

an autonomous driving control apparatus configured to monitor a stress state of the driver using the biometric information of the driver measured by the one or more sensors, to compare an allowable jerk of the driver calculated based on a jerk at a time point at which the stress state of the driver exceeds a preset reference value and a predicted jerk calculated based on location and movement information of the vehicle and the preceding vehicle measured while the vehicle travels, and to output an alarm signal based on a driving state of the vehicle when the predicted jerk exceeds the allowable jerk of the driver; and an interface configured to output information that corresponds to the alarm signal.

* * * * *